United States Patent
Kang et al.

(10) Patent No.: US 12,211,203 B2
(45) Date of Patent: Jan. 28, 2025

(54) OPTICAL COHERENCE TOMOGRAPHY-BASED SYSTEM FOR DIAGNOSIS OF HIGH-RISK LESION AND DIAGNOSIS METHOD THEREFOR

(71) Applicants: THE ASAN FOUNDATION, Seoul (KR); UNIVERSITY OF ULSAN FOUNDATION FOR INDUSTRY COOPERATION, Ulsan (KR)

(72) Inventors: Soo Jin Kang, Seoul (KR); Hyun Seok Min, Suwon-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 330 days.

(21) Appl. No.: 17/633,113

(22) PCT Filed: Aug. 5, 2020

(86) PCT No.: PCT/KR2020/010331
§ 371 (c)(1),
(2) Date: Feb. 4, 2022

(87) PCT Pub. No.: WO2021/025459
PCT Pub. Date: Feb. 11, 2021

(65) Prior Publication Data
US 2022/0335601 A1    Oct. 20, 2022

(30) Foreign Application Priority Data
Aug. 5, 2019   (KR) .................. 10-2019-0095168

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0066* (2013.01); *A61B 5/02007* (2013.01);
(Continued)

(58) Field of Classification Search
None
See application file for complete search history.

(56) References Cited

U.S. PATENT DOCUMENTS 7,972,272 B2  7/2011  Munce et al.
9,285,209 B2  3/2016  Lim et al.
(Continued)

FOREIGN PATENT DOCUMENTS

KR   10-2009-0115728 A   11/2009
KR   10-2015-0053629 A   5/2015
(Continued)

OTHER PUBLICATIONS

International Search Report issued Nov. 9, 2020 in PCT/KR2020/010331 filed Aug. 5, 2020, 2 pages.
(Continued)

*Primary Examiner* — Soo Shin
(74) *Attorney, Agent, or Firm* — Oblon, McClelland, Maier & Neustadt, L.L.P.

(57) ABSTRACT

The disclosure purposes to provide an optical coherence tomography (OCT)-based system for diagnosing a high risk lesion such as a vulnerable atheromatous plaque by using an artificial intelligence model through deep learning. A deep learning-based diagnostic method of diagnosing a high risk lesion of a coronary artery includes: acquiring an OCT image of a coronary artery lesion of a patient; extracting a first feature of a thin cap from the OCT image; setting a region of interest included in the OCT image on a basis of the first feature; and determining whether the region of interest includes a high risk lesion.

11 Claims, 12 Drawing Sheets

(51) Int. Cl.
 A61B 5/02 (2006.01)
 G16H 30/40 (2018.01)
 G16H 50/20 (2018.01)

(52) U.S. Cl.
 CPC .......... *A61B 5/7267* (2013.01); *A61B 5/7275* (2013.01); *A61B 5/7278* (2013.01); *A61B 5/7485* (2013.01); *G16H 30/40* (2018.01); *G16H 50/20* (2018.01); *G06T 2207/10101* (2013.01); *G06T 2207/20081* (2013.01); *G06T 2207/30048* (2013.01); *G06T 2207/30096* (2013.01); *G06T 2207/30101* (2013.01)

(56) References Cited

U.S. PATENT DOCUMENTS

| | | | |
|---|---|---|---|
| 9,959,622 | B2 | 5/2018 | Kim et al. |
| 2006/0265043 | A1* | 11/2006 | Mandrusov ............... A61F 2/86 623/1.42 |
| 2018/0310888 | A1* | 11/2018 | Itu .......................... G16H 50/50 |
| 2019/0159737 | A1* | 5/2019 | Buckler ............... A61B 6/5217 |
| 2020/0327664 | A1* | 10/2020 | Wilson ................ G06F 18/2431 |
| 2020/0364855 | A1* | 11/2020 | Ha .......................... G16H 50/30 |
| 2022/0277456 | A1* | 9/2022 | Woolf .................. G06V 10/764 |

FOREIGN PATENT DOCUMENTS

| | | |
|---|---|---|
| KR | 10-2016-0012038 A | 2/2016 |
| WO | WO 2019/104217 A1 | 5/2019 |

OTHER PUBLICATIONS

Bae, Y. et al., "Prediction of coronary thin-cap fibroatheroma by intravascular ultrasound-based machine learning", 2019 (online publication date May 4, 2019), Atherosclerosis, vol. 288, pp. 168-174, total 8 pages.

Jun, T. et al., "Automated detection of vulnerable plaque in intravascular ultrasound images", 2019 (online publication date Nov. 14, 2018), Medical & Biological Engineering & Computing, vol. 57, pp. 863-876, total 15 pages.

Jang, I. et al., "In Vivo Characterization of Coronary Atherosclerotic Plaque by Use of Optical Coherence Tomography", 2005, Circulation, vol. 111, No. 12, pp. 1551-1555, total 7 pages.

Grant of Patent (Office Action) dated Jul. 21, 2021 in Korean Application 10-2019-0095168 filed on Aug. 5, 2019, total 8 pages, with translation).

Notification of Reason for Refusal (Office Action) dated Nov. 11, 2020 in Korean Application 10-2019-0095168 filed on Aug. 5, 2019, total 11 pages, with translation).

\* cited by examiner

FIG. 5

| | |
|---|---|
| Clinical data | |
| Age, years | 65.5±9.7 |
| Men | 451 (75%) |
| Diabetes mellitus | 168 (28%) |
| Hypertension | 367 (61%) |
| Current smoker | 276 (46%) |
| Hyperlipidemia | 343 (57%) |
| Acute coronary syndrome | 162 (27%) |
| Quantitative angiographic data | |
| Involved vessel | |
| Left anterior descending artery lesion | 331 (55%) |
| Left circumflex artery lesion | 144 (24%) |
| Right coronary artery lesion | 187 (31%) |
| Diameter stenosis, % | 51.9±12.8 |
| Minimal lumen diameter, mm | 1.6±0.5 |
| Lesion length, mm | 17.5±10.4 |
| Proximal refereence lumen diameter, mm | 3.4±0.5 |
| Distal reference lumen diameter, mm | 2.9±0.7 |

FIG. 9

| | AUC# | Sensitivity (recall) | Specificity | PPV (precision) | NPV | Overall accuracy |
|---|---|---|---|---|---|---|
| Training samples (5-fold CV) | | | | | | |
| Group 1 | 0.962 | 88.3% | 93.3% | 51.4% | 99.0% | 93.0% |
| Group 2 | 0.951 | 85.6% | 91.3% | 43.8% | 98.8% | 90.8% |
| Group 3 | 0.967 | 85.4% | 94.5% | 55.2% | 98.8% | 93.8% |
| Group 4 | 0.971 | 90.7% | 90.6% | 43.4% | 99.2% | 90.6% |
| Group 5 | 0.966 | 93.3% | 89.5% | 41.5% | 99.4% | 89.8% |
| Average of 5 groups* | 0.963±0.008 | 88.7±3.4% | 91.8±2.0% | 47.1±5.9% | 99.0±0.3% | 91.6±1.7% |
| Test samples | | | | | | |
| Within the lesion | 0.962 | 88.6% | 93.2% | 50.8% | 99.0% | 92.8% |
| In the entire OCT pullback | 0.955 | 88.6% | 91.3% | 18.3% | 99.7% | 91.3% |

OPTICAL COHERENCE TOMOGRAPHY-BASED SYSTEM FOR DIAGNOSIS OF HIGH-RISK LESION AND DIAGNOSIS METHOD THEREFOR

TECHNICAL FIELD

The disclosure relates to an artificial intelligence (AI) system for simulating functions such as recognition, decision, and the like of a human brain using a machine learning algorithm, and an application thereof.

In detail, the disclosure relates to a system for diagnosing a high risk lesion on coronary artery on the basis of an optical coherence tomography.

BACKGROUND ART

Recently, artificial intelligence systems for implementing human-level intelligence are being used in various fields. Unlike the existing rule-based smart system, the artificial intelligence system is a system in which a machine learns and judges by itself and becomes smarter. The more the artificial intelligence system is used, the better a recognition rate and the more accurate understanding of user preferences. Accordingly, the existing rule-based smart system has gradually been replaced by a deep learning-based artificial intelligence system. Artificial intelligence technologies may include machine learning, for example, deep learning, and component technologies using the machine learning.

Atherosclerosis refers to a vascular disease in which cholesterol is deposited on an endothelium that mainly covers the innermost part of blood vessels, and atheroma is formed as a result of endothelial cell proliferation. The inside of the atheroma is thin like porridge, and a surrounding area thereof is surrounded by a hard fibrous cap called "plaque." When atherosclerotic plaque becomes unstable, it ruptures forming a thrombus (blood cake) in the blood vessel. In addition, when bleeding occurs into the atheroma, the inner diameter of the blood vessel is rapidly narrowed or the blood vessel is rather completely clogged, resulting in impaired blood circulation to the periphery.

The rupture of the atherosclerotic plaque (atheromatous plaque) in the cardiovascular system and the thrombus formation accompanying thereto are the main causes of acute coronary syndrome. It is very important to diagnose the above-described atherosclerotic plaques, in particular, vulnerable atheromatous plaques that is prone to rupture, for example, thin cap fibroatheroma (TCFA), and predict the prognosis of myocardial infarction, sudden death, and the like.

However, accurate identification of TCFA requires reading training for experts, and it takes a lot of time because hundreds of cross-sectional images per blood vessel are read one by one. Furthermore, there have been limitations in obtaining quantitative information on TCFA quickly and accurately during cardiovascular procedures in the prior art.

DESCRIPTION OF EMBODIMENTS

Technical Problem

Provided is an optical coherence tomography (OCT)-based system for diagnosing high risk lesions such as vulnerable atheromatous plaques using an artificial intelligence model through deep learning.

However, such an objective is exemplary, and the scope of the present disclosure is not limited thereby.

Solution to Problem

According to an aspect of the disclosure, a deep learning-based diagnostic method of diagnosing a high risk lesion of a coronary artery includes an image acquiring step of acquiring an optical coherence tomography (OCT) image of a coronary artery lesion of a patient, a feature extraction step of extracting a first feature of a thin cap from the OCT image, a region-of-interest setting step of setting a region of interest included in the OCT image on a basis of the first feature, and a high risk determination step of determining whether the region of interest includes a high risk lesion.

Furthermore, the first feature may include information about a fibrous cap thickness (FCT), the feature extraction step may further include a step of extracting a second feature about a necrotic core from the OCT image, and the high risk determination step may include determining whether the region of interest includes a thin cap fibroatheroma (TCFA), on a basis of the first feature and the second feature.

Furthermore, the region-of-interest setting step may include indicating a marker corresponding to the region of interest.

Furthermore, the deep learning-based diagnostic method may further include, when the OCT image is determined to include a high risk lesion, a lesion display step of displaying a lesion indicating a region corresponding to the high risk lesion, wherein the region corresponding to the high risk lesion includes a region including a thin cap fibroatheroma (TCFA).

Furthermore, the lesion display step may be performed by using at least one of a Grad-CAM and a guided Grad-CAM.

According to another aspect of the disclosure, a deep learning-based diagnostic apparatus of diagnosing a high risk lesion of a coronary artery includes an image acquiring unit configured to acquire an optical coherence tomography (OCT) image of a coronary artery lesion of a patient, a feature extraction unit configured to extract a first feature of a thin cap from the OCT image, a region-of-interest setting unit configured to set a region of interest included in the OCT image on a basis of the first feature, and a high risk determination unit configured to determine whether the region of interest includes a high risk lesion.

Other aspects, features, and advantages than those described above will become apparent from the following drawings, claims, and detailed descriptions to embody the disclosure below.

Advantageous Effects of Disclosure

According to an embodiment of the disclosure configured as above, it is possible to evaluate the microstructure of coronary artery atherosclerotic plaque (cholesterol chunks) through an optical coherence tomography (OCT) image having a high resolution.

In other words, a deep learning apparatus for diagnosing a high risk lesion through the OCT of the disclosure has the effect of evaluating atherosclerotic plaque even in a nearly clogged coronary artery using a less-thick tube, and of more accurately distinguishing a thrombus with a high resolution.

Furthermore, by using the OCT, the occurrence of thrombosis or restenosis, which can occur after a coronary artery interventional therapy, may be prevented, and a vascular response after the therapy may be evaluated more accurately.

It is possible to quickly and accurately diagnose vulnerable atherosclerotic plaques because the OCT images of many specimens are used as training data (or training samples) for deep learning, and it can be of great help to treat coronary artery disease by finding out in advance atherosclerotic plaques that are prone to rupture.

The scope of the disclosure is not limited by the above effects.

BRIEF DESCRIPTION OF DRAWINGS

FIG. 5 illustrates samples and baseline characteristics for learning an artificial intelligence model, according to an embodiment of the disclosure.

FIG. 9 illustrates the high risky lesion diagnosis performance of an artificial intelligence model, according to an embodiment of the disclosure.

MODE OF DISCLOSURE

Figure 1:
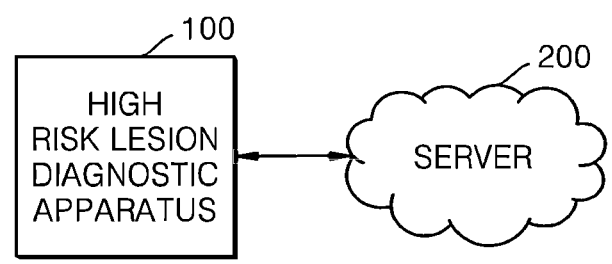
FIG. 1 is a system diagram of a high risk lesion diagnosis system according to an embodiment of the disclosure.

Hereinafter, various embodiments of the disclosure will be described with reference to the accompanying drawings. Various embodiments of the disclosure can make various changes and can have various embodiments, and specific embodiments are illustrated in the drawings and related detailed descriptions are described. However, this is not intended to limit the disclosure to particular modes of practice, and it is to be appreciated that various modifications, equivalents, and/or alternatives that do not depart from the spirit and technical scope of the disclosure are encompassed in the disclosure. Throughout the drawings, like reference numerals denote like elements.

It will be further understood that the terms "comprises" and/or "comprising" used in various embodiments of the disclosure specify the presence of the disclosed functions, operations, or constituent elements, but do not preclude the presence or addition of one or more functions, operations, or constituent elements. Furthermore, in various embodiments of the disclosure, it is to be understood that the terms such as "comprises" and/or "comprising" are intended to indicate the existence of the features, numbers, steps, actions, components, parts, or combinations thereof disclosed in the specification, and are not intended to preclude the possibility that one or more features, numbers, steps, actions, components, parts, or combinations thereof may exist or may be added.

In various embodiments of the disclosure, expressions such as "or" include any and all combinations of the words listed together. For example, "A or B" may include A, may include B, or may include both A and B.

Expressions such as "first", "second", "1st", or "2nd" used in various embodiments of the disclosure may modify various constituent elements of various embodiments, but do not limit the corresponding constituent elements. For example, the above terms are used herein merely to describe a variety of constituent elements regardless of an order and/or importance. The above terms may be used to distinguish one constituent element from another constituent element For example, a first user device and a second user device are both user devices and may denote different user devices. For example, without departing from the right scope of various embodiments of the disclosure, a first constituent element may be referred to as a second constituent element, and vice versa.

It will be understood that when a component (e.g., a first component) is referred to as being "(operatively or communicatively) coupled to/with" or "connected to/with" another component (e.g., a second component), it may be coupled to/with or connected to/with the other component directly or indirectly through one or more other components (e.g., third components). On the other hand, when a component (e.g., a first component) is referred to as being "directly coupled to/with" or "directly connected to/with" another component (e.g., a second component), no other components (e.g., third components) exist therebetween.

In an embodiment of the disclosure, terms such as "module", "unit", and "part" may signify a unit to process at least one function or operation and the unit may be embodied by hardware, software, or a combination of hardware and software. Furthermore, a plurality of "module", "unit", "part", etc. are integrated into at least one of a module or a chip, and can be implemented as at least one processor, except when each needs to be implemented with individual specific hardware.

Terms used in various embodiments of the disclosure are only used to describe a specific embodiment, and are not intended to limit the various embodiments of the disclosure. An expression used in a singular form in the specification also includes the expression in its plural form unless clearly specified otherwise in context.

Unless defined otherwise, all terms used herein including technical or scientific terms have the same meanings as those generally understood by those of ordinary skill in the art to which the disclosure may pertain.

The terms as those defined in generally used dictionaries are construed to have meanings matching that in the context of related technology and, unless clearly defined otherwise, are not construed to be ideally or excessively formal.

Hereinafter, various embodiments of the disclosure are described in detail, with reference to the accompanying drawings.

FIG. 1 is a system diagram of a high risk lesion diagnosis system 100 according to an embodiment of the disclosure.

The high risk lesion diagnostic apparatus 100 is an apparatus for predicting and diagnosing an ischemia lesion generated on the coronary artery of a patient.

Whether it is a high risk lesion may be checked through the presence of a thin fibrous cap atheromatous plaque (hereinafter, referred to as the thin cap fibroatheroma (TCFA)). In detail, the presence of TCFA is a separate predictor from other indexes such as FFR and the like in relation with a negative heart result. In particular, a TCFA-containing lesion has a correlation to the increased risk of distal embolization and periprocedural myocardial infarction in a coronary artery interventional therapy.

In this state, TCFA has the characteristics of a large necrotic core, foamy macrophage infiltration, and a fibrous cap having a thickness of 65 µm or less.

The high risk lesion diagnostic apparatus 100 of the disclosure may use optical coherence tomography (hereinafter, OCT) including information about fibrous cap thickness (hereinafter, FCT) to identify whether it is a TCFA-containing lesion.

In detail, the high risk lesion diagnostic apparatus 100 of the disclosure may automatically perform OCT subdivision, tissue classification, and atheroma detection through back-propagation using deep learning, for example, a convolution neural network (CNN). Accordingly, the high risk lesion diagnostic apparatus 100 may diagnose whether the lesion is a high risk lesion including TCFA.

The OCT of the disclosure has a resolution of about 10 times higher than that of an existing intravascular ultrasound so that it is possible to evaluate the microstructure of coronary artery atherosclerotic plaque (cholesterol chunks).

An intravascular ultrasound method according to the related art has a limitation in evaluating an atherosclerotic plaque of a microstructure. The deep learning apparatus 100 for diagnosing a high risk lesion through the OCT of the disclosure has effects of evaluating atherosclerotic plaque in a coronary artery that is almost clogged, by using a tube having a much smaller thickness, and showing a high resolution to accurately distinguish blood clots.

In addition to the accurate evaluation of a coronary artery lesion and the finding of blood clots and unstable atherosclerosis plaque, the features of OCT may include preventing thrombosis or restenosis that may be generated after a coronary artery interventional therapy and accurately evaluating a blood vessel reaction after the procedure.

A server 200 may include at least one external server for training and updating an artificial intelligence (AI) model and performing prediction through the AI model.

The server 200 according to an embodiment of the disclosure may include an AI model for extracting a vascular border image from an OCT image.

In this state, when an OCT image is input, the AI model may output whether a coronary artery lesion is a high risk lesion containing TCFA. In this state, the AI model may consider morphological features, computational features, and clinical features on the OCT image.

The AI model may be intensively trained on whether a lesion included in an OCT image is TCFA or a mimic TCFA. In this regard, detailed descriptions are presented later.

Although FIG. 1 illustrates that the high risk lesion diagnostic apparatus 100 and the server 200 are implemented as separate elements, according to an embodiment of the disclosure, the high risk lesion diagnostic apparatus 100 and the server 200 may be implemented as one element. In other words, according to an embodiment, the high risk lesion diagnostic apparatus 100 may be an on-device AI apparatus that directly trains and updates an AI model. In the following description, for convenience of explanation, the high risk lesion diagnostic apparatus 100 is assumed to be an on-device AI apparatus.

Figure 2:
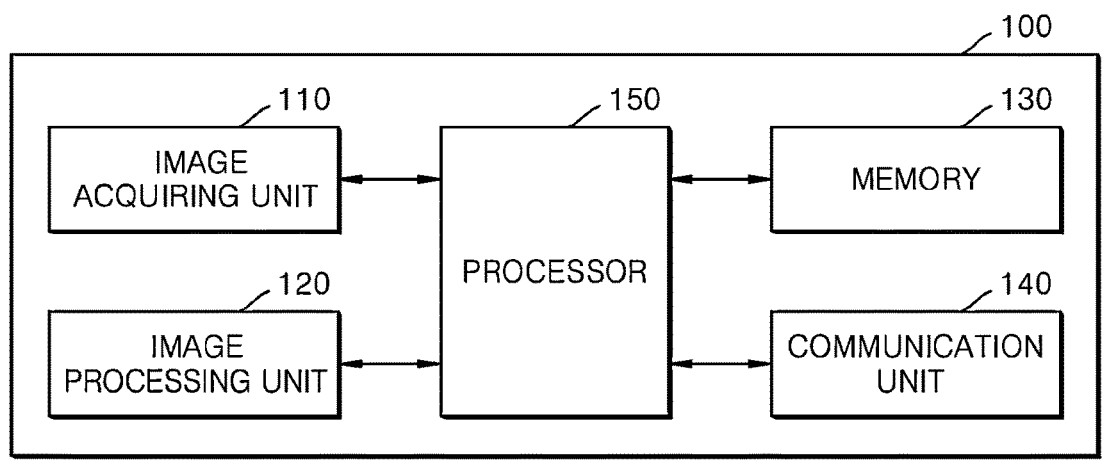
FIG. 2 is a schematic block diagram of the constituent element of a high risk lesion diagnostic apparatus according to an embodiment of the disclosure.

FIG. 2 is a schematic block diagram of the constituent element of the high risk lesion diagnostic apparatus 100 according to an embodiment of the disclosure.

Referring to FIG. 2, the high risk lesion diagnostic apparatus 100 may include an image acquiring unit 110, an image processing unit 120, a memory 130, a communication unit 140, and a processor 150 that is electrically connected to and controls the above-described constituent elements.

The image acquiring unit 110 may acquire OCT image data through various sources. For example, the image acquiring unit 110 may be implemented as a commercial scanner to acquire OCT images by scanning the inside of a coronary artery. The image data acquired through the image acquiring unit 110 may be processed in the image processing unit 120.

The image processing unit 120 may perform processing on the image data acquired through the image acquiring unit 110. In the image processing unit 120, various image processing such as decoding, scaling, noise filtering, frame rate conversion, resolution conversion, or the like may be performed on the image data.

The memory 130 may store various data for the overall operation of the high risk lesion diagnostic apparatus 100, for example, a program and the like for processing or controlling by the processor 150. The memory 130 may store a plurality of application programs or applications executed in the high risk lesion diagnostic apparatus 100, and data and instructions for the operation of the high risk lesion diagnostic apparatus 100. At least some of the application programs may be downloaded from an external server through a wireless communication.

Also, at least some of the application programs may be present on the high risk lesion diagnostic apparatus 100, from the time of shipment, for the basic functions of the high risk lesion diagnostic apparatus 100. An application program may be stored in the memory 130 and executed by the processor 150 to perform the operation or functions of the high risk lesion diagnostic apparatus 100. In particular, the memory 130, as an example, may be implemented as an internal memory such as ROM, RAM, and the like included in the processor 150, or implemented as a memory separated from the processor 150.

The communication unit 140 may be configured to communicate with various types of external devices according to various types of communication methods. The communication unit 140 may include at least one of a WiFi chip, a Bluetooth chip, a wireless communication chip, and a near field communication (NFC) chip. The processor 150 may perform a communication with the server 200 or various external apparatuses by using the communication unit 140.

In particular, when a WiFi chip or a Bluetooth chip is used, various pieces of connection information such as SSID, a session key, and the like are first transceived to establish a communication, and then, various pieces of information may be transceived. A wireless communication chip may refer to a chip that performs a communication according to various communication standards such as IEEE, Zigbee, 3rd generation (3G), 3rd generation partnership project (3GPP), long term evolution (LTE), and the like. An NFC chip may refer to a chip that operates in an NFC method using a 13.56 MHz band among various RF-ID frequency bands such as 135 kHz, 13.56 MHz, 433 MHz, 860-960 MHz, 2.45 GHz, and the like.

The processor 150 may generally control the high risk lesion diagnostic apparatus 100. In detail, the processor 150 controls the overall operation of the high risk lesion diagnostic apparatus 100 by using various programs stored in the memory 130 of the high risk lesion diagnostic apparatus 100. For example, the processor 150 may include a central processing unit (CPU), random access memory (RAM), read-only memory (ROM), and a system bus. The ROM is configured to store an instruction set for system booting, and the CPU, in response to the instructions stored in the ROM, copies an operating system (O/S) stored in the memory of the high risk lesion diagnostic apparatus 100 to the RAM, and executes the O/S to boot the system. When booting is completed, the CPU copies the various applications stored in the memory 130 to the RAM, and executes the various applications to perform various operations. In the above description, the processor 150 is described as including one CPU only, but the processor 150 may be implemented as a plurality of CPUs (or DSP, SoC, and the like).

According to an embodiment of the disclosure, the processor 150 may be implemented by a digital signal processor (DSP) for processing a digital signal, a microprocessor, or a time controller (TCON). However, the disclosure is not limited thereto, and the processor 150 may include one or more of a CPU, a micro controller unit (MCU), a micro processing unit (MPU), a controller, an application processor (AP), or a communication processor (CP), an ARM processor, or may be defined by a corresponding term. Furthermore, the processor 150 may be implemented by a system on chip (SoC) including a processing algorithm or large scale integration (LSI), or in the form of a field programmable gate array (FPGA).

Figure 3:
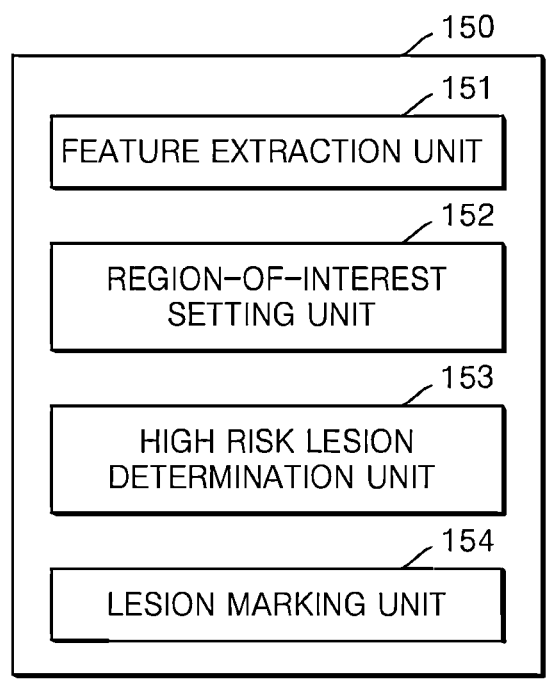
FIG. 3 is a block diagram of the internal configuration of a processor, according to an embodiment of the disclosure.

FIG. 3 is a block diagram of the internal configuration of a processor, according to an embodiment of the disclosure.

Referring to FIG. 3, the processor 150 of the disclosure may include a feature extraction unit 151, a region-of-interest setting unit 152, a high risk lesion determination unit 153, and a lesion marking unit 154.

The feature extraction unit 151, the region-of-interest setting unit 152, the high risk lesion determination unit 153, and the lesion marking unit 154 of the disclosure may be implemented through a separate software module stored in the memory 130 and driven by the processor 150. Each software module may perform one or more functions and operations described in this specification. Furthermore, the respective elements may be implemented as separate modules, or as one module.

As described above, according to another embodiment of the disclosure, the feature extraction unit 151, the region-of-interest setting unit 152, the high risk lesion determination unit 153, and the lesion marking unit 154 may be elements included in a processor (not shown) included in the server 200.

Figure 4:
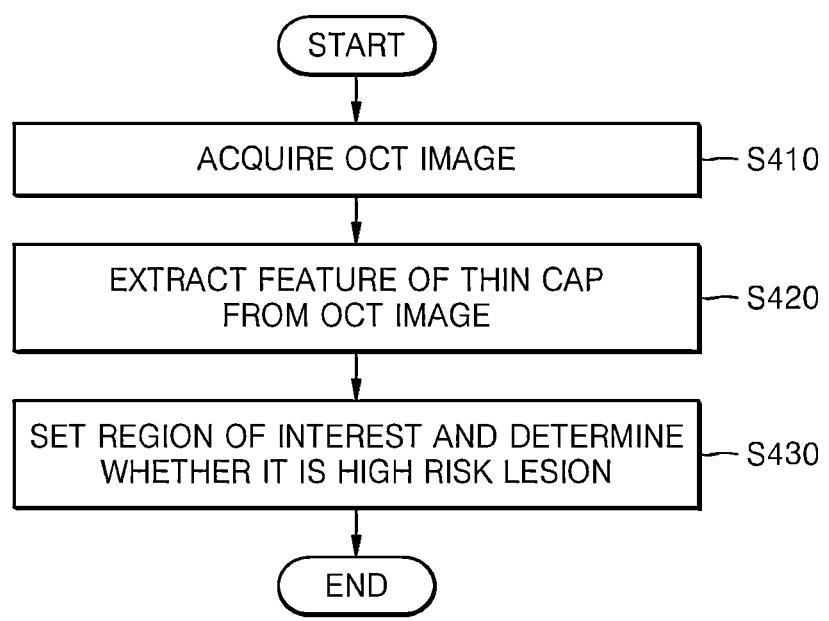
FIG. 4 is a flowchart of a high risk lesion diagnostic method using optical coherence tomography (OCT) image data according to an embodiment of the disclosure.

FIG. 4 is a flowchart of a high risk lesion diagnostic method using OCT image data according to an embodiment of the disclosure.

In the following description, the diagnostic method of the disclosure is described with reference to FIGS. 2 to 4 together.

The image acquiring unit 110 of the disclosure may acquire OCT image data (S410). The OCT image was acquired while pulling back a catheter at a speed of 20 mm/s after administration of nitroglycerin. In this state, a lesion may include a plaque having the maximum thickness of 0.5 mm or more.

In this state, the OCT is a non-invasive imaging technique that analyzes the signal obtained from a white optical interference system, thereby acquiring an image of the internal structure of a biological sample with a high resolution close to the resolution of a microscope.

Also, the OCT image data may include information about a large lipid-rich core, a thin fibrous cap covering an atherosclerotic plaque (thickness<65 μm), whether macrophages appearing during active inflammation are included in the fibrous cap (macrophages localized in the fibrous cap), neovascularization, etc.

The feature extraction unit 151 may extract a feature of a thin cap from the acquired OCT image data (S420). However, this is merely an example, and the feature extraction unit 151 may extract a feature of a necrotic core.

In detail, the feature extraction unit 151 may extract a feature through an AI model that is trained to extract a plurality of features included in the OCT image by using a plurality of OCT images as training data. In this state, the AI model may include a CNN, but this is merely an embodiment, and may include various neural networks such as a generative adversarial network (GAN), a deep neural network (DNN), a recurrent neural network (RNN), a bidirectional recurrent deep neural network (BRDNN), and the like.

The region-of-interest setting unit 152 may set a region of interest on the basis of the feature of a thin cap extracted by the feature extraction unit 151 (S420), and the high risk lesion determination unit 153 may determine whether a lesion is a high risk lesion including TCFA on the basis of the information about not only the feature of a thin cap, but also the feature of a necrotic core (S430).

The lesion marking unit 154 may mark a region of interest included in an OCT image, and furthermore mark a region including TCFA. In this state, the lesion marking unit 154 may mark by using at least one of gradient-weighted class activation mapping (Grad-CAM) and guided Grad-CAM.

In this state, the Grad-CAM is a modified or improved version of CAM, and recognizes the importance of each neuron to a target label by using the gradient information input to the last convulsion layer in the CNN. The CAM is applicable only to an AI model using global average pooling, but the Grad-CAM has no problem at all. The Grad-CAM that obtains an average for each feature map may obtain a vector using the number of feature maps as a length, and accordingly, a hit map calculation is possible.

The Grad-CAM is a method of giving a score to each entry by using a backpropagation-based filter weight and a convulsion output value regarding the reason on which an AI model such as a CNN determines a review to be positive (or negative). When the convulsion output value provides a source for determining a result, the filter weight performs a function of highlighting a material provided by convulsion depending on a class. In other words, the Grad CAM may interpret a model by inversely using a process of training a region to be visualized.

FIG. 5 illustrates samples and baseline characteristics for learning an AI model, according to an embodiment of the disclosure.

A coronary artery lesion was searched for 602 patients from May 2010 to May 2016, and OCT data was acquired. In this state, all patients had at least one lesion of angiographic stenosis of 30%-85%. Then, the patients were randomly divided into a training sample (n=480) and a test sample (n=122) at a ratio of 4:1. Furthermore, data of 65 non-duplicated patients who received pre-OCT from Feb. 1, 2016 to Nov. 30, 2017 was used additionally.

35,678 OCT image frames were obtained from 480 training samples, and 9,722 OCT image frames were obtained from 122 test samples. Each OCT image frame had an interval of 0.4 mm, and was classified according to the presence of TCFA.

In detail, a necrotic core of 90° or more and FCT of 65 μm are assigned as a threshold of TCFA. Both the necrotic core and calcification are characterized by a weak signal region, but the necrotic core and the calcification are differentiated by sharp margins and diffusion in the weak signal region. Accumulation of macrophages may be identified by the location of abundant spots with tail shadows in a layer deep behind a macrophages surface band.

Figure 6:
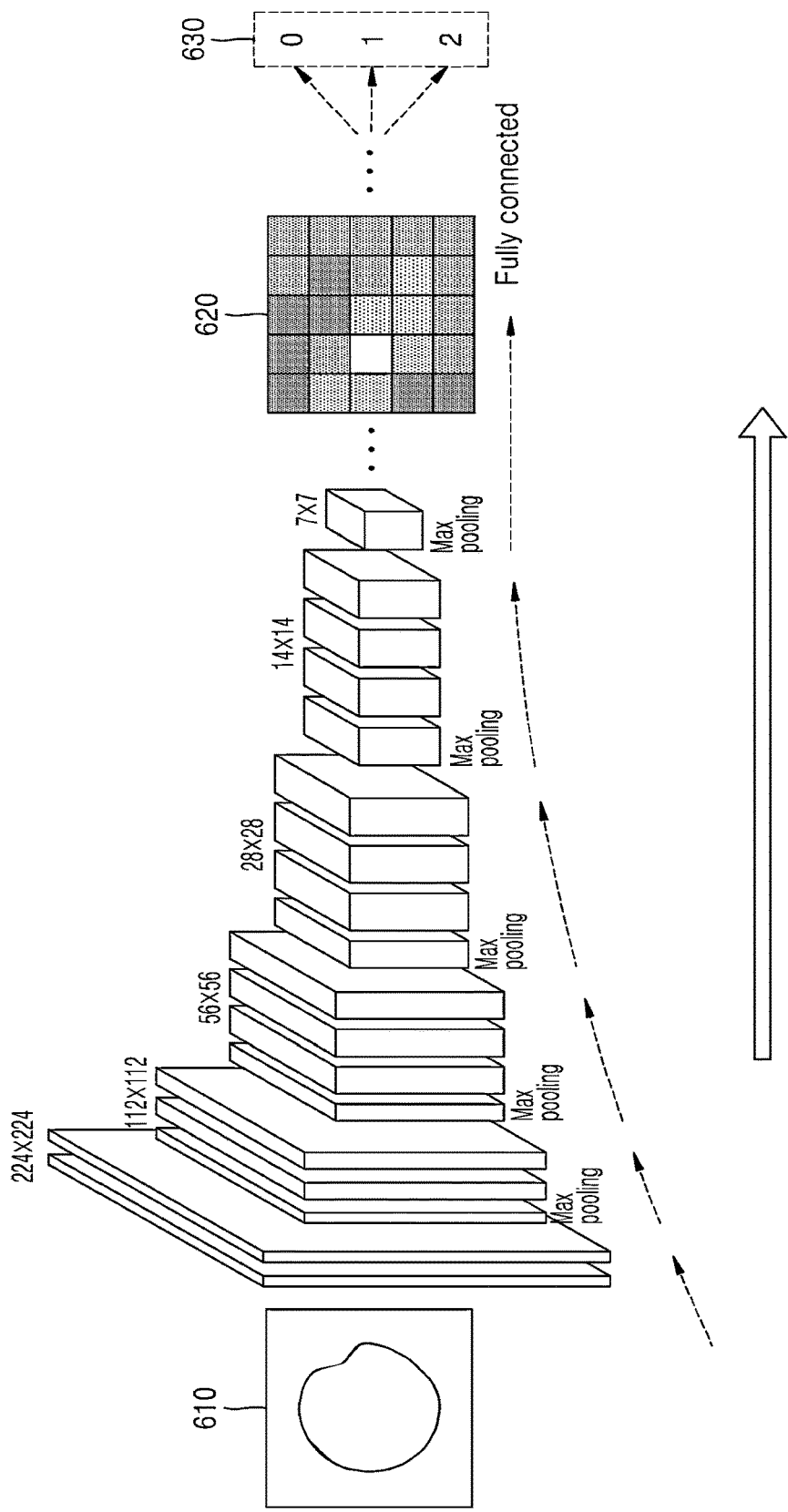
FIG. 6 illustrates a process that is performed when the OCT data is input to a convolution neural network (CNN)-based artificial intelligence model, as training data, according to an embodiment of the disclosure.

FIG. 6 illustrates a process that is performed when the OCT data is input to a CNN-based AI model, as training data, according to an embodiment of the disclosure.

When an OCT image 610 is input to the CNN-based application in the high risk lesion diagnostic apparatus 100 of the disclosure, the high risk lesion diagnostic apparatus 100 may obtain a feature map of an image input through a first layer included in the CNN.

In this state, the first layer may be a convulsion layer that generates a feature map of an image input by using a convulsion filter or a weight set on the basis of a result of training through a plurality of images in the server 200, but the disclosure is not limited thereto, and the above-described process may be performed in the high risk lesion diagnostic apparatus 100. In other words, when an AI model is configured as an embedded system in the high risk lesion diagnostic apparatus 100, there is a need to reduce a storage capacity by compressing a feature map. To compress and store a plurality of feature maps, the high risk lesion diagnostic apparatus 100 may convert and encode the generated feature map through a lookup table. The high risk lesion diagnostic apparatus 100 may store in the memory a feature map 620 that is encoded to have a reduced storage capacity, and decode the feature map stored in the memory, when necessary. In this state, the memory may be a memory included in the high risk lesion diagnostic apparatus 100, or a memory included in an external apparatus or an external server.

The AI model of the disclosure may output a classification result 630 through a fully connected layer on the basis of the feature map 620 obtained by convulsing the OCT image 610. For example, the AI model may output 0 when an OCT image has no hardened atheromatous plaque, output 1 when an OCT image has a hardened atheromatous plaque, but has no high risk lesion, and output 2 when an OCT image has a high risk lesion including TCFA. However, this is merely an example, and according to an example, the AI model may output 0 when no TCFA is present, and output 1 when a high risk lesion including TCFA is present.

To distinguish an OCT image including TCFA, all layers of the entire CNN may be finely adjusted through back-propagation in the entire network. In detail, the initial learning rate is adjusted to 0.0002 by using an Adam optimizer, and random sampling, Gaussian noise, elastic deformation, and vertical/horizontal flip were used.

FIGS. 7A to 8B show OCT images on which regions of interest and Grad-CAMs are marked by an AI model, according to an embodiment of the disclosure.

Figure 7A:
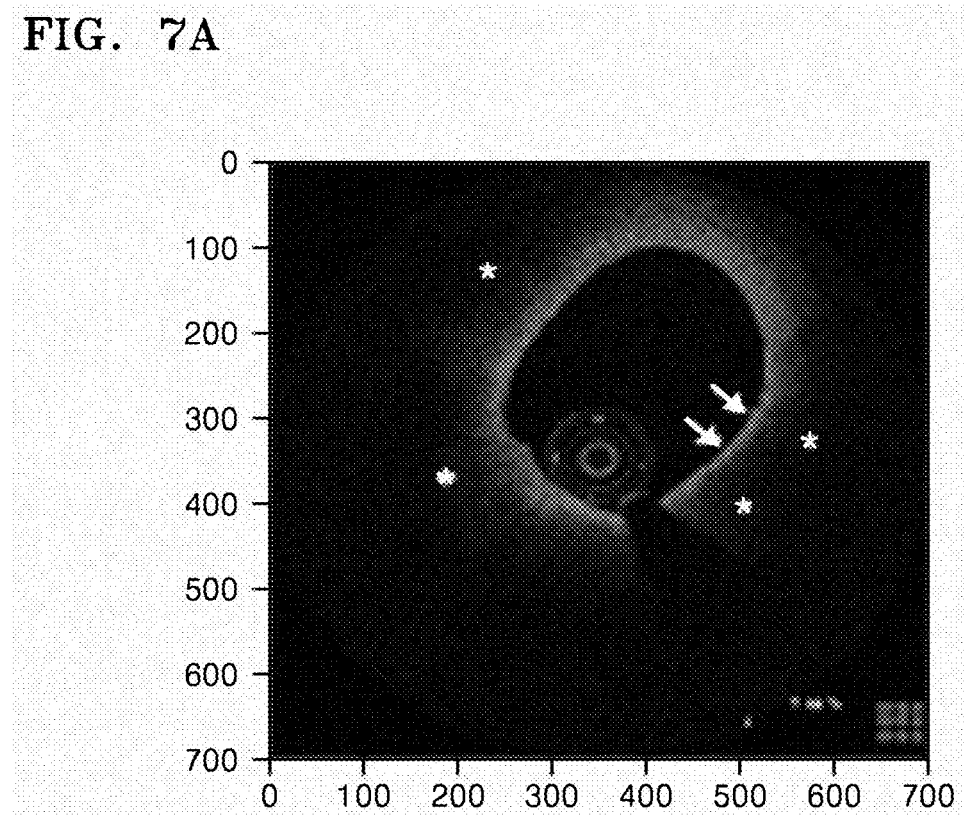
FIGS. 7A to 8B show OCT images on which regions of interest and gradient-weighted class activation mappings (Grad-CAM) are marked by an artificial intelligence model, according to an embodiment of the disclosure.
Figure 8A:
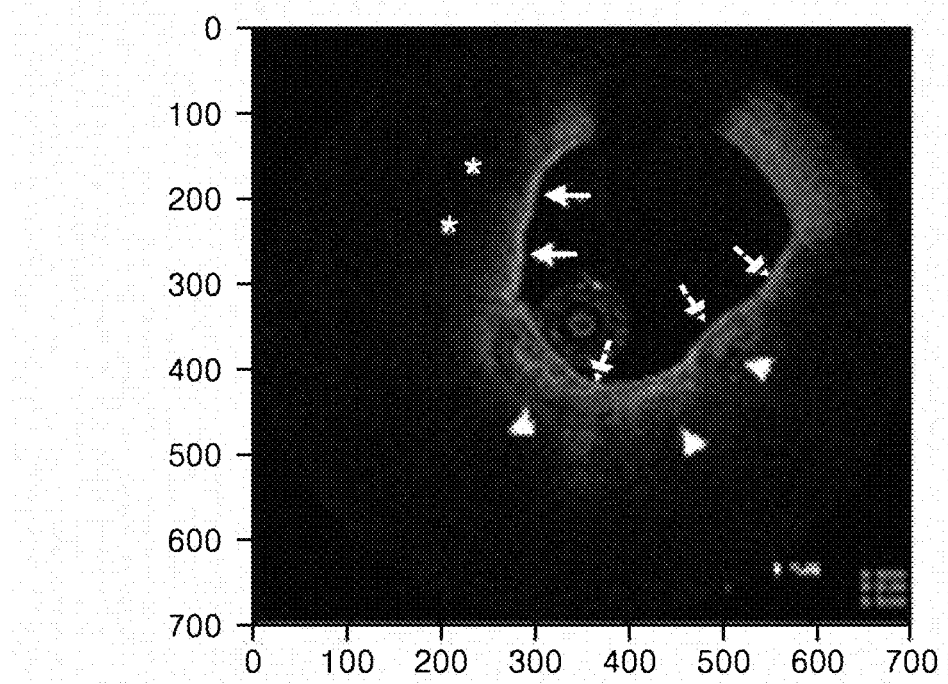

Referring to the OCT images of FIG. 7A and FIG. 8A, the high risk lesion diagnostic apparatus 100 may indicate a marker corresponding to a region of interest. In detail, a solid arrow and a dashed arrow indicated outwards in a vascular lumen indicate portions of a thin cap in a blood vessel marked by the AI model. Furthermore, a white asterisk (*) indicates a necrotic core.

In this state, the AI model may be trained to extract a portion where a cap has a thickness is 65 μm or less, as a feature of the thin cap, but the disclosure is not limited thereto.

Referring to the OCT image of FIG. 7A, it may be seen that a portion indicated by the solid arrow is a portion formed of a thin cap, and a necrotic core is present at a portion indicated by the white asterisk. As described above, the morphological feature of a vulnerable hardened atheromatous plaque, for example, TCFA, refers to a case in which a thin fibrous cap covers a large lipid-rich core or a necrotic core.

Accordingly, the high risk lesion diagnostic apparatus 100 of the disclosure may determine that a portion in which a solid arrow (thin cap) and a white asterisk (necrotic core) are simultaneously indicated is where TCFA is present.

Figure 7B:
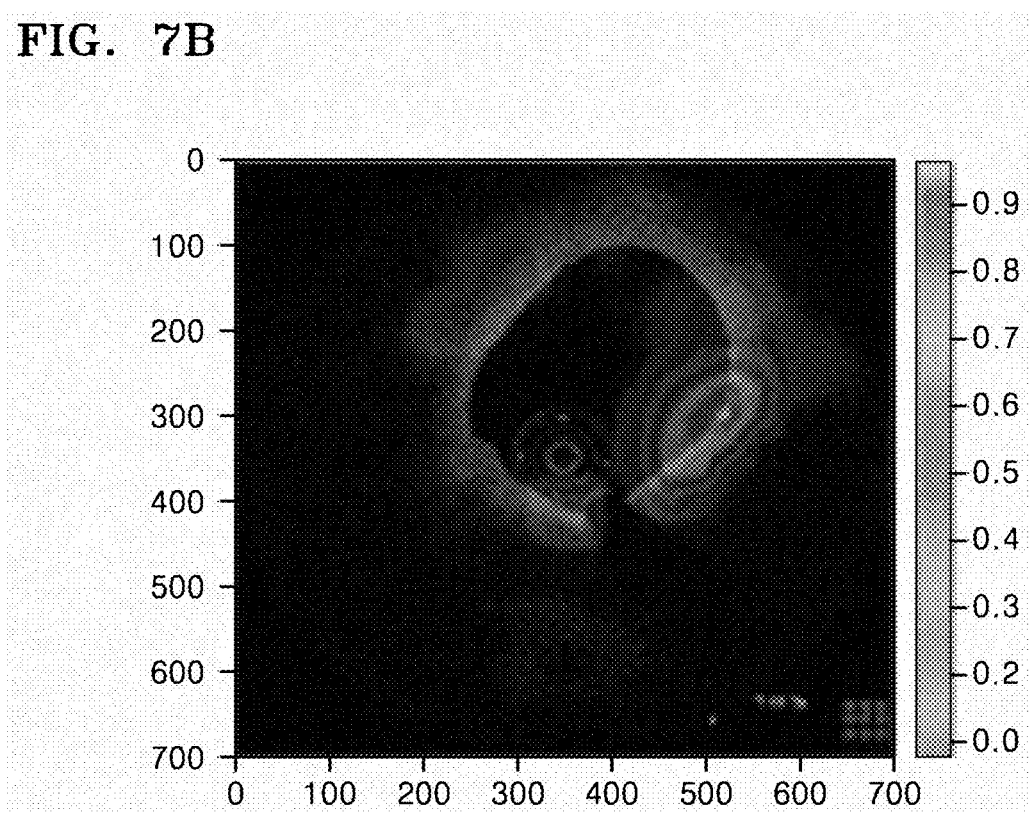

FIG. 7B shows that a Grad-CAM is indicated for a portion where TCFA is present, on the basis of the region of interest of FIG. 7A.

The high risk lesion diagnostic apparatus 100, as an example, the lesion marking unit 154, of the disclosure may use the Grad-CAM that is a visualization technique, to indicate the presence of TCFA. A gradient is sued to evaluate the importance of a space location of a convulsion layer, and the Grad-CAM may regenerate a location map that provides highlight to a region of interest of an OCT image. When a threshold of a region is greater than 0.8, the region is coded in red and regarded as a core region.

The AI model of the disclosure may indicate a red coded region of a gradient as a high risk lesion that requires attention. In FIG. 7B, it may be seen that a high risk lesion such as TCFA is present in the 3 o'clock or 4 o'clock direction.

As in the OCT image of FIG. 8A, it may be seen that a portion indicated by a solid arrow or a dashed arrow is a portion formed of a thin cap, and a necrotic core is present in a portion indicated by a white asterisk. A white triangle in a direction from the outside of a vascular lumen to the inside means a calcified portion, not a necrotic core.

As described above, the morphological feature of a vulnerable hardened atheromatous plaque, for example, TCFA, refers to a case in which a thin fibrous cap covers a large lipid-rich core or a necrotic core. In other words, even when a region is formed of a thin cap, if the thin cap covers a calcified portion, the region is not classified as TCFA.

In other words, in the OCT image of FIG. 8A, a portion indicated by a dashed arrow (5 o'clock or 7 o'clock direction) is formed of a thin cap, but the portion covers a calcified portion and is not classified as TCFA. In contrast, a portion indicated by a solid arrow (9 o'clock or 11 o'clock direction) is formed of a thin cap, and includes a necrotic core, and thus the portion is classified as TCFA.

Figure 8B:
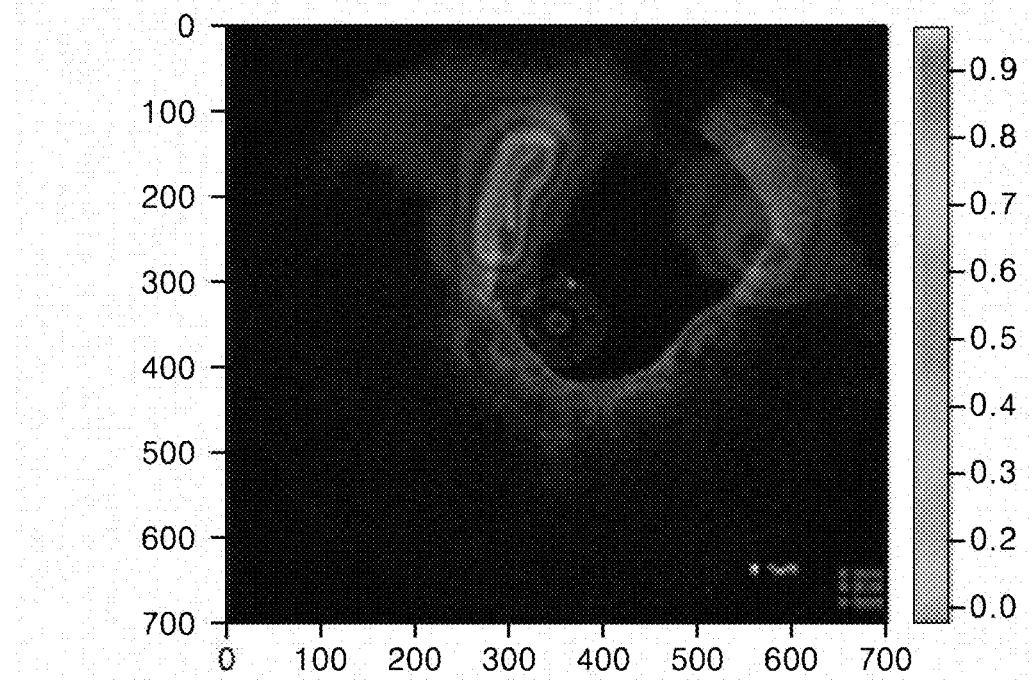

FIG. 8B shows that Grad-CAM is indicated to a portion including TCFA on the basis of the region of interest like FIG. 8A. The AI model of the disclosure may indicate a red coded region of the gradient as a high risk lesion that requires attention. In FIG. 8B, it may be seen that a high risk lesion such as TCFA is present in the 9 o'clock or 11 o'clock direction.

FIG. 9 illustrates the high risky lesion diagnosis performance of an AI model, according to an embodiment of the disclosure.

Referring to FIG. 9, a deep learning model or an AI model that performs a 5-fold cross validation on training samples showed, when there is a lesion, an overall accuracy of 91.6±1.7%, a sensitivity of 88.7±3.4%, and a specificity of 91.8±2.0% (AUC 0.96±0.01). When there is a lesion in the test sample, the overall accuracy was 92.8% (AUC 0.96), and for an overall pullback image, the overall accuracy was 91.3% (AUC 0.96). When cross-section level performance of each blood vessel is averaged, the sensitivity was 94.5±14.6%, the specificity was 92.8±9.2%, and the overall accuracy was 92.9±7.9%.

Most activated maps among the images classified as those where TCFA is present are located at TFC above a necrotic core. In the deep learning process, a gradient-based Grad CAM analysis may provide a class-discriminative visualization map for prediction. The red-coded activation map is located in a thin cap covering most of a lipid core, through which a TCFA-containing lesion may be distinguished.

Figure 10:
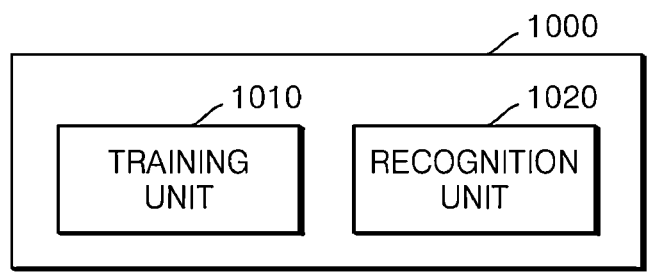
FIG. 10 is a block diagram of a training unit and a recognition unit, according to various embodiments of the disclosure.

FIG. 10 is a block diagram of a training unit 1010 and a recognition unit 1020, according to various embodiments of the disclosure.

Referring to FIG. 10, a processor 1000 may include at least one of the training unit 1010 and the recognition unit 1020. The processor 1000 of FIG. 10 may correspond to the processor 150 of the high risk lesion diagnostic apparatus 100 of FIG. 2 or a processor (not shown) of the server 200.

The training unit 1010 may generate or train a recognition model having a certain standard for determining a situation. The training unit 1010 may generate a recognition model having a determination standard using collected training data.

As an example, the training unit 1010 may generate, train, or update an object recognition model having a standard for determining whether a TCFA is present in a vascular lumen included in an OCT image by using various OCT images as training data.

In another example, the training unit 1010 may generate, train, or update a model having a standard for determining whether a TCFA is present in an input image by using various morphological features and clinical features of TCFA as training data.

The recognition unit 1020 may estimate target data by using certain data as input data of a trained recognition model.

As an example, the recognition unit 1020 may acquire (or estimate or infer) a Grad-CAM display image about a TCFA included in an image by using various OCT images as input data of a trained recognition model.

In another example, the recognition unit 1020 may estimate (or determine or infer) the presence of a TCFA by applying the TCFA feature and clinical feature included in various OCT images to a trained recognition model.

At least part of the training unit 1010 and at least part of the recognition unit 1020 may be implemented as software modules or manufactured in the form of at least one hardware chip to be mounted on an electronic apparatus. For example, at least part of the training unit 1010 and the recognition unit 1020 may be manufactured in the form of a dedicated hardware chip for AI, or manufactured as part of an existing general purpose processor, for example, a CPU or an application processor, or a graphics dedicated processor, for example, a GPU, to be mounted on the above-described various electronic apparatuses or object recognition apparatus. In this state, the dedicated hardware chip for AI is a dedicated processor specialized in probability calculation and has higher parallel processing performance than that of an existing general purpose processor, thereby quickly processing computational tasks in the AI fields such as machine learning.

When the training unit 1010 and the recognition unit 1020 are implemented as software modules or program modules including instructions, the software modules may be stored in a computer-readable non-transitory computer readable media. In this case, the software module may be provided by an operating system (OS) or by a certain application. Alternatively, part of the software module may be provided by an OS, and the other may be provided by a certain application.

In this case, the training unit 1010 and the recognition unit 1020 may be mounted on a single electronic apparatus, or respectively in separate electronic apparatuses. For example, one of the training unit 1010 and the recognition unit 1020 may be included in the high risk lesion diagnostic apparatus 100, and the other may be included in the server 200. Furthermore, the training unit 1010 and the recognition unit 1020 may provide, by a wired or wireless method, model information established by the training unit 1010 to the recognition unit 1020, or the data input to the recognition unit 1020 may be provided to the training unit 1010 as additional training data.

The above-described methods according to various embodiments of the disclosure may be implemented in the form of an application that is installable on a high risk lesion diagnostic apparatus.

Furthermore, the above-described methods according to various embodiments of the disclosure may be implemented through only software upgrade or hardware upgrade with respect to a high risk lesion diagnostic apparatus.

Furthermore, the above-described various embodiments of the disclosures may be performed through the embedded server included in the high risk lesion diagnostic apparatus 100, or through the external server of the high risk lesion diagnostic apparatus 100.

According to an embodiment of the disclosure, various embodiments described below may be implemented as software including instructions stored in a computer-readable or an apparatus similar thereto-readable recording medium, by using software, hardware, or a combination thereof. In some cases, the embodiments described in this specification may be implemented by a processor by itself. According to software implementation, embodiments such as procedures and functions described in this specification may be implemented as separate software modules. Each of the software modules may perform one or more functions and operations described herein.

A computer or an apparatus similar thereto may include an apparatus capable of calling stored instructions from a storage medium and operating according to the called instructions, and may include an apparatus according to the disclosed embodiments. When the command is executed by the processor, the processor may perform directly, or under the control of the processor, a function corresponding to the command using other constituent elements. The command may include codes generated or executed by a compiler or an interpreter.

An apparatus-readable recording medium may be provided in the form of a non-transitory computer-readable recording medium. Here, "non-transitory" merely means that the storage media do not contain signals and are tangible, but do not distinguish data being semi-permanently or temporarily stored in the storage media. In this state, a non-transitory computer-readable medium refers to a medium that stores data semi-permanently, rather than a medium that stores data for a short moment, such as registers, caches, and memory, and can be read by a device. Detailed examples of the non-transitory computer-readable medium include CDs, DVDs, hard disks, Blu-ray disks, USBs, memory cards, ROMs, and the like.

As such, although the disclosure has been described with reference to the embodiment shown in the drawings, this is merely exemplary, and those of ordinary skill in the art will understand that various modifications and other equivalent embodiments are possible therefrom. Accordingly, the true technical protection scope of the disclosure should be determined by the technical concept of the appended claims.

The invention claimed is:

1. A deep learning-based diagnostic method of diagnosing a high risk lesion of a coronary artery, the deep learning-based diagnostic method comprising:

acquiring, by a high risk lesion diagnostic apparatus, an optical coherence tomography (OCT) image of a coronary artery lesion of a patient;

extracting, by the high risk lesion diagnostic apparatus, a first feature of a thin cap and a second feature about a necrotic core from the OCT image using an artificial intelligence (AI) model;

setting, by the high risk lesion diagnostic apparatus, a region of interest included in the OCT image according to whether the first feature satisfies a preset first reference; and determining, by the high risk lesion diagnostic apparatus, whether the region of interest includes a high risk lesion according to whether the second feature satisfies a preset second reference, wherein the AI model is trained to receive a plurality of OCT images as input data, extract a plurality of features included in the OCT image for each of the plurality of OCT images, and output a feature map indicating whether to include the high risk lesion based on the plurality of features and a result value, as output data, the AI model adjusts an initial learning rate by an Adam optimizer, and a training data set including the input data and the output data is classified according to whether the high risk lesion has been classified, and a result of the classification is evaluated and repeatedly trained.

2. The deep learning-based diagnostic method of claim 1, wherein
the determining is to determine whether the region of interest includes a thin cap fibroatheroma (TCFA), on a basis of the first feature and the second feature, and
the preset first reference is information about a thickness and the preset second reference is information about an angle of the necrotic core.

3. The deep learning-based diagnostic method of claim 1, wherein the setting comprises indicating a marker corresponding to the region of interest using the AI model.

4. The deep learning-based diagnostic method of claim 1, further comprising, when the OCT image is determined to include a high risk lesion, displaying a lesion indicating a region corresponding to the high risk lesion, wherein
the region corresponding to the high risk lesion comprises a region including a thin cap fibroatheroma (TCFA).

5. The deep learning-based diagnostic method of claim 4, wherein the displaying is performed by using at least one of a Grad-CAM and a guided Grad-CAM.

6. A non-transitory computer-readable recording medium storing therein an operating program that causes a computer to execute a process comprising:

acquiring an optical coherence tomography (OCT) image of a coronary artery lesion of a patient;

extracting a first feature of a thin cap and a second feature about a necrotic core from the OCT image using an artificial intelligence (AI) model;

setting a region of interest included in the OCT image according to whether the first feature satisfies a preset first reference; and determining whether the region of interest includes a high risk lesion according to whether the second feature satisfies a preset second reference, wherein the AI model is trained to receive a plurality of OCT images as input data, extract a plurality of features included in the OCT image for each of the plurality of OCT images, and output a feature map indicating whether to include the high risk lesion based on the plurality of features and a result value, as output data, the AI model adjusts an initial learning rate by an Adam optimizer, and a training data set including the input data and the output data is classified according to whether the high risk lesion has been classified, and a result of the classification is evaluated and repeatedly trained.

7. The non-transitory computer-readable recording medium of claim 6, wherein
the determining is to determine whether the region of interest includes a thin cap fibroatheroma (TCFA), on a basis of the first feature and the second feature, and
the preset first reference is information about a thickness and the preset second reference is information about an angle of the necrotic core.

8. The non-transitory computer-readable recording medium of claim 6, wherein the setting comprises indicating a marker corresponding to the region of interest using the AI model.

9. The non-transitory computer-readable recording medium of claim 6, wherein the process further comprises, when the OCT image is determined to include a high risk lesion, displaying a lesion indicating a region corresponding to the high risk lesion, wherein
the region corresponding to the high risk lesion comprises a region including a thin cap fibroatheroma (TCFA).

10. The non-transitory computer-readable recording medium of claim 9, wherein the displaying is performed by using at least one of a Grad-CAM and a guided Grad-CAM.

11. An apparatus comprising:
processing circuitry configured to
acquire an optical coherence tomography (OCT) image of a coronary artery lesion of a patient,
extract a first feature of a thin cap and a second feature about a necrotic core from the OCT image using an artificial intelligence (AI) model,
set a region of interest included in the OCT image according to whether the first feature satisfies a preset first reference, and
determine whether the region of interest includes a high risk lesion according to whether the second feature satisfies a preset second reference, wherein
the AI model is trained to receive a plurality of OCT images as input data, extract a plurality of features included in the OCT image for each of the plurality of OCT images, and output a feature map indicating whether to include the high risk lesion based on the plurality of features and a result value, as output data,
the AI model adjusts an initial learning rate by an Adam optimizer, and
a training data set including the input data and the output data is classified according to whether the high risk lesion has been classified, and a result of the classification is evaluated and repeatedly trained.

* * * * *